US005726042A

United States Patent [19]

Shivakumar et al.

[11] Patent Number: 5,726,042

[45] Date of Patent: Mar. 10, 1998

[54] EXPRESSION OF HETEROLOGOUS PROTEINS IN *BACILLUS MEGATERIUM* UTILIZING SPORULATION PROMOTERS OF *BACILLUS SUBTILIS*

[75] Inventors: Annapur Gurulingappa Shivakumar, Libertyville; Leonard Katz, Waukegan; Lisa Beth Cohen, Lake Forest; Charles Lester Ginsburgh, Oak Forest; Leland Shawn Paul, Island Lake; Rita Irene Vanags, Hillside, all of Ill.

[73] Assignee: Abbott Laboratories, Abbott Park, Ill.

[21] Appl. No.: 722,695

[22] Filed: Sep. 30, 1996

Related U.S. Application Data

[63] Continuation of Ser. No. 349,141, Nov. 17, 1994, abandoned, which is a continuation of Ser. No. 187,778, Jan. 26, 1994, abandoned, which is a continuation of Ser. No. 46,111, Apr. 9, 1993, abandoned, which is a continuation of Ser. No. 933,604, Aug. 21, 1992, abandoned, which is a continuation of Ser. No. 571,007, Aug. 22, 1990, abandoned, which is a continuation of Ser. No. 178,746, Apr. 7, 1988, abandoned.

[51] Int. Cl.[6] .......... C12P 21/02; C12N 15/75; C12N 15/48; C12N 15/62

[52] U.S. Cl. .......... 435/69.1; 435/69.3; 435/172.3; 435/252.1; 435/252.31; 435/320.1; 530/350

[58] Field of Search .......... 435/69.1, 69.3, 435/252.1, 252.31, 172.3, 320.1; 530/350

[56] References Cited

U.S. PATENT DOCUMENTS

| | | | |
|---|---|---|---|
| 4,554,250 | 11/1985 | McCullough | 435/252.31 |
| 4,769,323 | 9/1988 | Stephens et al. | 935/11 |
| 4,861,707 | 8/1989 | Ivanoff et al. | 435/5 |
| 5,175,098 | 12/1992 | Watanabe et al. | 435/69.3 |

FOREIGN PATENT DOCUMENTS

| | | |
|---|---|---|
| 0195285 | 9/1986 | European Pat. Off. . |
| 0202470 | 11/1986 | European Pat. Off. . |
| 0207459 | 1/1987 | European Pat. Off. . |
| 2142336 | 1/1985 | United Kingdom . |

OTHER PUBLICATIONS

Kieselburg et al. (1984), Bio/Technology, vol. 2, pp. 254–259.

Goldrick et al. (1983), J. Bact., vol. 155, pp. 1459–1462.

Ratner et al. (1985) "Complete nucleotide sequence of AIDS virus," Nature, vol. 313, pp. 277–284.

Gordon (1975) "Gels containing solubilisers," *Electrophoresis of proteins* (North Holland Pub. Co, Amsterdam) pp. 26–28.

Von Tersch et al (1983) "Megacinogenic plasmids of *Bacillus megateirum*," J. Bact. vol. 155, pp. 872–877.

Chang, et al., *Molecular Cloning and Gene Regulation in Bacilli*, pp. 159–169.

Hardy, et al., *Nature* , 293:481–483 (Oct. 8, 1981).

Palva, et al., *Gene*, 22:229–235 (1983).

Zuber, et al., *Cell*, 35:275–283 (Nov. 1983).

*Primary Examiner*—Nancy Degen

*Attorney, Agent, or Firm*—Andreas M. Danckers; Dianne Casuto

[57] ABSTRACT

Proteins heterologous to *B. megaterium* can be expressed in *B. megaterium* using a sporulation promoter from *B. subtilis*.

16 Claims, 10 Drawing Sheets

EXPRESSION OF HETEROLOGOUS PROTEINS IN *BACILLUS MEGATERIUM* UTILIZING SPORULATION PROMOTERS OF *BACILLUS SUBTILIS*

This application is a continuation of U.S. Ser. No. 08/349,141, filed Nov. 17, 1994, now abandoned, which is a continuation of U.S. Ser. No. 08/187,778, filed Jan. 26, 1994, now abandoned, which is a continuation of U.S. Ser. No. 08/046,111, filed Apr. 9, 1993, now abandoned, which is a continuation of U.S. Ser. No. 07/933,604, filed Aug. 21, 1992, now abandoned, which is a continuation of U.S. Ser. No. 07/571,007, filed Aug. 22, 1990, now abandoned, which is a continuation of U.S. Ser. No. 07/178,746, filed Apr. 7, 1988, now abandoned.

BACKGROUND

The present invention relates to the expression of proteins heterologous to *Bacillus megaterium* under the control of a sporulation promoter of *Bacillus subtilis* such as the spoVG promoter which promoter is also heterologous to *B. megaterium.*

The art is replete with techniques for the expression of proteins foreign ("heterologous") to microbial cells by transforming the cells with heterologous "structural" DNA molecules which code for the heterologous proteins. As with the case of the expression of proteins native ("homologous") to microbes, the expression of heterologous proteins requires "promoter" (or "control") DNA which regulates the expression of protein from the structural genes in question, homologous or heterologous as the case may be.

The specific molecular and biochemical requirements for efficient expression of a structural gene resulting in the synthesis of a protein and its recovery in a biologically usable form have not been reduced to an exact science. There are biological peculiarities of each structural gene, gene product, promoter and their host environment which often combine to make heterologous gene expression and protein recovery difficult or impossible.

The host cell into which heterologous genes are introduced has a substantial effect on the expression of heterologous genes. The most common bacterial host used is *Escherichia coli* which has been extensively characterized genetically and readily takes up foreign DNA. One of the disadvantages of using *E. coli*, however, is that the protein products from cloned genes are often subjected to extensive degradation. Another is the problem of a toxic effect of the gene product on the host resulting in poor growth of the host or poor expression of the gene. To some extent, researchers have been successful in creating a compatible environment by either modifying the host or the foreign DNA. Although *E. coli* has been accommodative in most cases, it has exhibited substantial problems in making and maintaining hydrophobic proteins. Extensive degradation of such proteins has been observed, and many times as these proteins are being made, *E. coli* cells cease to grow and may undergo eventual lysis. In such cases, a compatible host must be found which will remain healthy while the foreign protein is being made.

Thus, the amount of protein synthesized can vary widely from gene to gene depending on the regulatory sequences employed and on other factors that are not yet fully understood. The fate of a foreign protein is also dependent on the nature of the protein and the nature of the host cell. The foreign protein may accumulate in the cell as an inclusion body or an intracellular crystal, remain soluble in the cell, be secreted, or break down due to the activity of proteases.

Recently, *Bacillus subtilis* has been used with increasing frequency as a host cell. *B. subtilis* responds to a different set of regulatory signals for gene expression than *E. coli* and has offered several advantages for expressing some proteins, because it is nonpathogenic and can secrete proteins into the medium.

SUMMARY OF THE INVENTION

This invention involves the novel combination of a sporulation promoter, such as PspoVG, from *Bacillus subtilis*, and a structural gene for a protein heterologous to *Bacillus megaterium* which is under the control of and in proper reading frame with respect to the sporulation promoter. The sporulation promoter and the heterologous structural gene are part of a cloning vehicle which is used to transform *Bacillus megaterium* so that the heterologous protein can be expressed by the transformed *B. megaterium* in recoverable form and in good yield.

This invention also includes methods of protein production using such cloning vehicles, and to proteins, particularly hydrophobic proteins such as HIV-I gp41, produced according to these methods.

DETAILED DESCRIPTION OF THE INVENTION

The present invention involves the cloning of heterologous genes and their expression in the form of proteins in the gram positive organism *Bacillus megaterium*. These heterologous genes are in proper reading frame relative to and under the control of a *B. subtilis* sporulation specific promoter such as PspoVG carried on plasmid pVG1 (obtained from Dr. Richard Losick, Harvard University). The spoVG promoter was originally isolated from the chromosomal DNA of *B. subtilis*. Other sporulation promoters from *B. subtilis* which may be used to transform *B. megaterium* consistent with the teachings of this invention include but are not limited to the spoOH, spoOA, spoIID promoters, and any other *B. subtilis* sporulation promoters that are specifically utilized during the stationary phase in the growth cycle of *B. megaterium* transformed with vectors carrying structural genes directed by such promoters.

Figure 1:
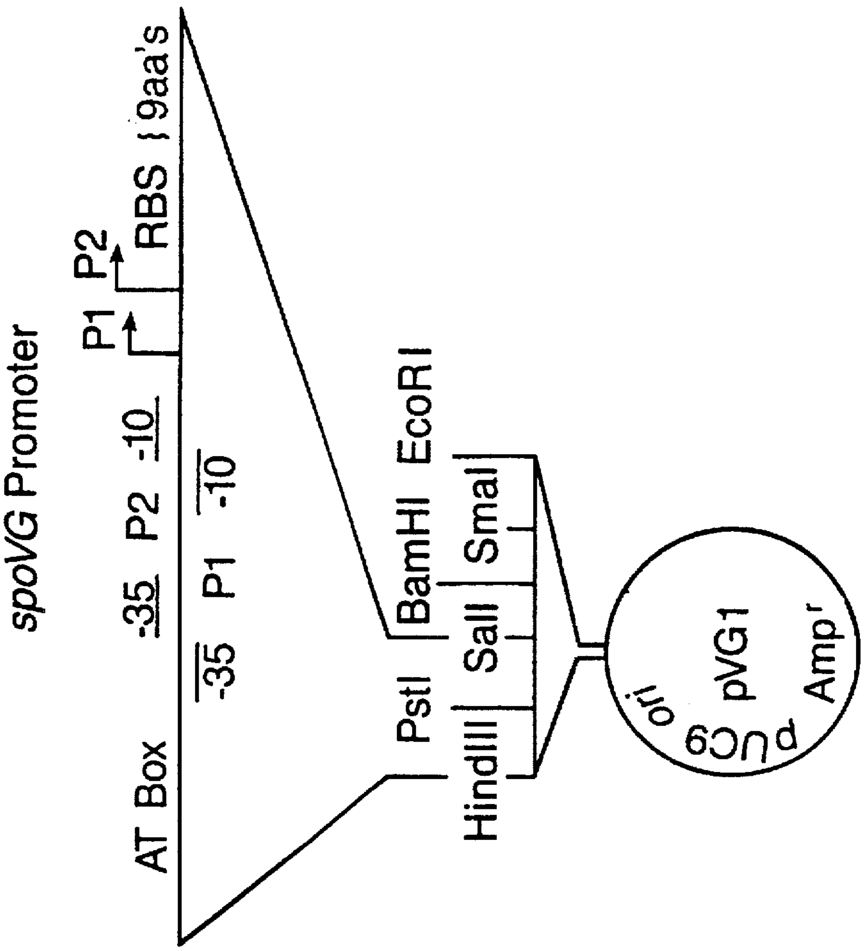
FIG. 1 is a physical map of plasmid pVG1 wherein a 157 bp HindIII-SalI fragment containing the spoVG promoter and codons for 9 N-terminal amino acids was cloned into the HindIII-SalI sites of pUC9.
Figure 2:
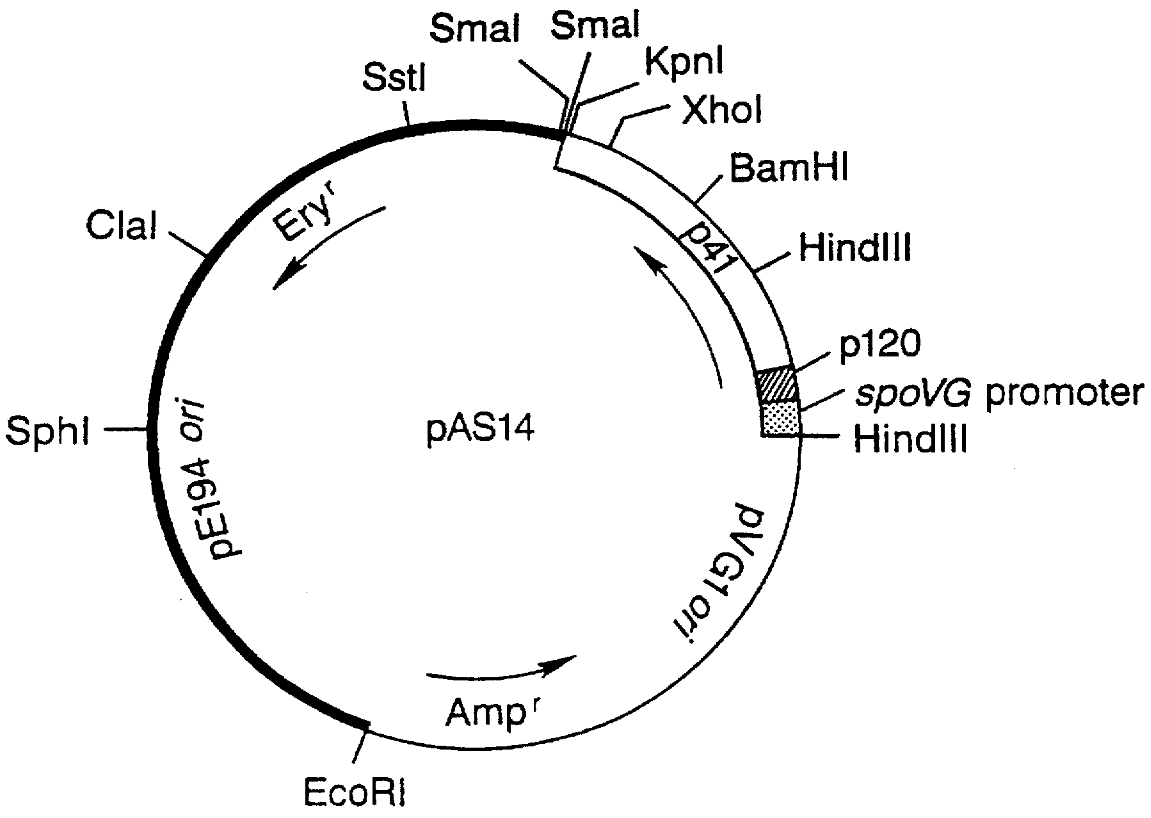
FIG. 2 is a physical map of plasmid pAS14 containing DNA coding for expression of 41spf-1 wherein the cross hatched block represents the C-terminus of HIV-I gp120, and the dotted block represents the spoVG promoter and the nine N-terminal amino acids coding portion of the gene specifying the spoVG protein. The thick line represents the DNA fraction from the *B. subtilis* plasmid pE194, and the thin line represents DNA from the plasmid pVG1.

Specifically, in one embodiment of this invention, plasmid DNA from *B. subtilis* pE194[1] is ligated with plasmid DNA from *E. coli* (pVG1) (which contains the spoVG promoter) to produce a multifunctional plasmid pAS5. An expression vector (pAS14; FIG. 2; Example 3) is then constructed by opening up the plasmid pAS5 at a SalI site (located after the ninth N-terminal amino acid codon in spoVG) gene, and inserting the heterologous structural gene. In an illustrative embodiment of this invention, the 1.4 kb SalI-EcoRI DNA fragment containing the entire gene for HIV-I gp41 and about 45 C-terminal amino acids of HIV-I gp120 (Ratner et al., *Nature*, 313:277–284 (1985)) is inserted as the heterologous structural gene in such a way that HIV-I gp41 is synthesized as a fusion protein with a portion of gp120 under the control of the spoVG promoter once *B. megaterium* is transformed with pAS14. Other heterologous structural genes can be inserted in lieu of gp41, including, but not limited to genes which code for fragments of gp41 which nonetheless react with antibodies to gp41.

[1] pE194, pUB110 and pC194 plasmids are basically natives of another organism namely *Staphylococcus aureus*. These plasmids have been introduced into *B. subtilis* successfully where they replicate and express resistance to corresponding antibiotics. See "Construction and properties of chimeric plasmids in *B. subtilis*." Gryczan and Dubnau, PNAS, 75:1428–1432 (1978).

In this embodiment, the *B. subtilis* plasmid pE194 is employed since it confers erythromycin resistance, so the transformed cells can be selected for erythromycin resistance. The antibiotic selection marker erythromycin can be replaced by a kanamycin resistance determinant (e.g. pUB110; Example 10), by a chloramphenicol resistance determinant (e.g. pC194; Example 13) or by other selection markers well known in the art. Although pAS14, pCR2 and pCR5 are exemplified in this invention, it should be apparent to those skilled in the art that other variations are possible, by way of replacing the antibiotic resistance marker genes, by altering the spoVG promoter or the ribosomal binding sequences to enhance protein expression, or the like. Furthermore, conservative substitutions of amino acids in polypeptides can be introduced by changing codons in the structural DNA, without affecting the biological activity of the polypeptides. All such modifications are included within the scope of this invention.

Figure 5:
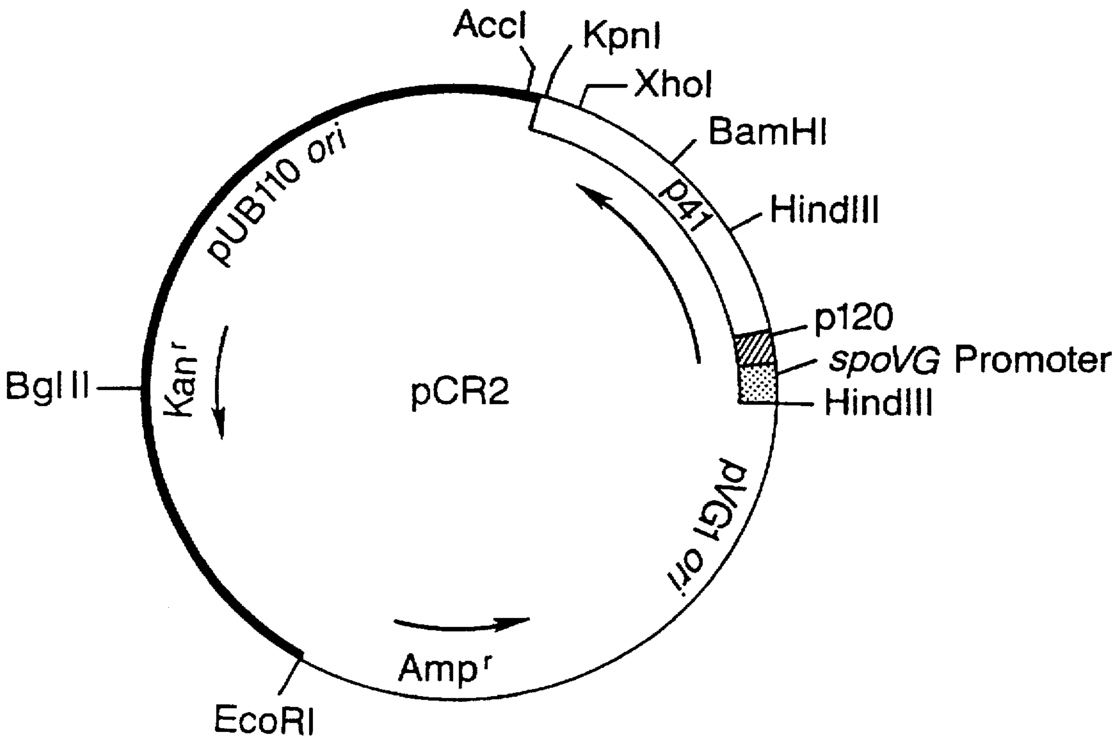
FIG. 5 is a physical map of plasmid pCR2 containing DNA coding for the expression of 41spf-1, where the cross hatched block represents the coding sequence of the C-terminus of HIV-I gp120, the dotted block represents the spoVG promoter and the nine N-terminal amino acid coding portion of the gene specifying the spoVG protein and 4 amino acids produced from DNA fusions, the thick line represents the DNA from the *B. subtilis* plasmid pUB110, and the thin line represents DNA from the plasmid pVG1. Arrows show the direction of transcription of each gene.
Figure 6:
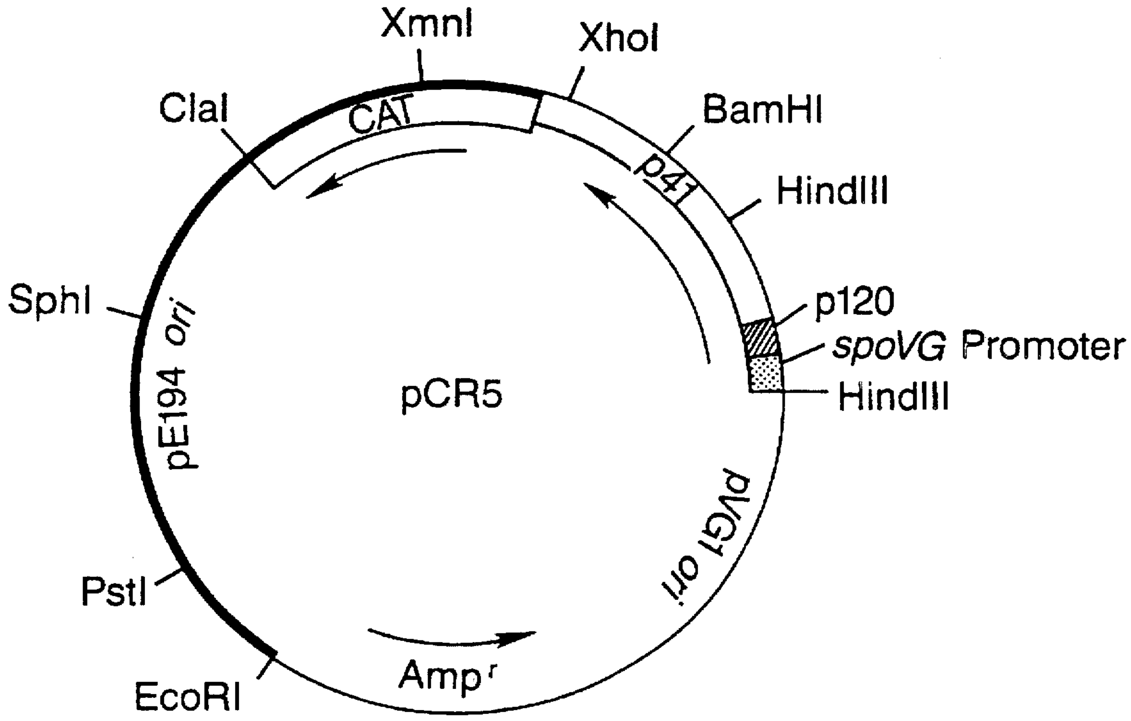
FIG. 6 is a physical map of plasmid pCR5 containing DNA coding for the expression of 41spf-1 wherein the cross hatched block represents The coding sequence of the C-terminus of HIV-Igp120, the dotted block represents the spoVG promoter and the nine N-terminal amino acid coding portion of the gene specifying the spoVG protein and four amino acids produced from DNA fusions, the wider open block represents the chloramphenicol acetyl transferase (cat) gene containing insert, the thick line represents the *B. subtilis* plasmid DNA portion, and the thin line represents DNA from the plasmid pVG1. Arrows show the direction of transcription of each gene.

In the embodiment represented by FIGS. 2, 5 and 6, the present invention provides for expression of a polypeptide (hereinafter referred to as 41spf-1) having an amino acid sequence represented by the following formula:

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| M | E | V | T | D | V | R | L | R | V | D | R | R | I | F | R | P | G | G | G | D | M | R | D | N | W | R | S | E |
| L | Y | K | Y | K | V | V | K | I | E | P | L | G | V | A | P | T | K | A | K | R | R | V | V | | | | | |
| Q | R | E | K | R | A | V | G | I | G | A | L | F | L | G | F | L | G | A | A | G | S | T | M | | | | | |
| G | A | A | S | M | T | L | T | V | Q | A | R | Q | L | L | S | G | I | V | Q | Q | Q | N | N | | | | | |
| L | L | R | A | I | E | A | Q | Q | H | L | L | Q | L | T | V | W | G | I | K | Q | L | Q | A | | | | | |
| R | I | L | V | V | E | R | Y | L | K | D | Q | Q | L | L | G | I | W | G | C | S | G | K | L | | | | | |
| I | C | T | T | A | V | P | W | N | A | S | W | S | N | K | S | L | E | Q | I | W | N | W | F | | | | | |
| M | T | W | M | E | W | D | R | E | I | N | N | Y | T | S | L | I | H | S | L | I | E | E | S | | | | | |
| Q | N | Q | Q | K | K | N | E | Q | E | L | L | E | L | D | K | W | A | S | L | W | N | W | F | | | | | |
| N | I | T | N | W | L | W | Y | I | K | L | F | I | M | I | V | G | G | L | V | G | L | R | I | | | | | |
| V | F | A | V | L | S | V | V | N | R | V | R | Q | G | Y | S | P | L | S | F | Q | T | H | L | | | | | |
| P | I | P | R | G | P | D | R | P | E | G | I | E | E | E | G | G | E | R | D | R | D | R | S | | | | | |
| I | R | L | V | N | G | S | L | A | L | I | W | D | D | L | R | S | L | C | L | F | S | Y | H | | | | | |
| R | L | R | D | L | L | L | I | V | T | R | I | V | E | L | L | G | R | R | G | W | E | A | L | | | | | |
| K | Y | W | W | N | L | L | Q | Y | W | S | Q | E | L | K | N | S | A | V | S | L | L | N | A | | | | | |
| T | A | I | A | V | A | E | G | T | D | R | V | I | G | V | V | Q | G | A | Y | R | A | I | R | | | | | |
| H | I | P | R | R | I | R | Q | G | L | E | R | I | L | L | | | | | | | | | | | | | | |

The polypeptide above is produced in the bacterial host *B. megaterium* under the control of the spoVG promoter. Fragments or fusion polypeptides including the amino acids of the sequence described above that elicit antibodies against the AIDS virus or react with AIDS antibodies can also be produced.

The present invention further provides for the development of specific diagnostic reagents to test for the presence of antibodies to the AIDS virus in humans. In the embodiments of Examples 9, 12 and 17, the fusion polypeptides of the present invention appear as insoluble material comprised of a short C-terminal HIV-I gp120 portion followed by the entire HIV-I gp41 protein and can be purified by any one or more of the methods that are known in the art. These may include detergent solubilization, gel electrophoresis, chromatography, etc. The polypeptides of the present invention also could provide for development of vaccines to provide immunity against AIDS virus infection in humans.

GENERAL METHODS

Illustrative of the general methods employed in this invention, the cloning and expression of the gene for the transmembrane envelope protein gp41 can be performed as follows:

Competent Cells and Transformation

Standard procedures are used for preparation of competent cells and transformation of *E. coli* (Maniatis et al., Molecular Cloning, A Laboratory Manual. Cold Spring Harbor Laboratory, Cold Spring Harbor, N.Y. (1982)) and *B. subtilis* (Contente and Dubnau, Characterization of Plasmid Transformation in *Bacillus subtilis*. Kinetic Properties and the Effect of DNA Conformation., *Mol. Gen. Genet.* 167:251–258 (1979)).

Plasmid DNA is isolated from small cultures of selected colonies by alkaline hydrolysis (as described by Maniatis, et al. in "*Molecular Cloning*". Cold Spring Harbor, 1982, p. 368; Hofemeister et al., *Mol. Gen. Genet.* 189:58–68 (1983)) is analyzed by restriction digestions and gel electrophoresis. Restriction enzymes are used according to suppliers instructions. Standard conditions for use of restriction enzymes employed at least 2 units of enzyme for each ug of DNA to be digested and sufficient incubation time (usually 1–2 hours) to allow complete digestion of the DNA.

Transformation in *B. megaterium*

Transformation in *B. megaterium* is performed according to the modified method of VonTersch and Carlton, Megacinogenic Plasmids of *Bacillus megaterium*. *J. Bacteriol.* 155:872–877 (1983). *B. megaterium* strain PV361 is grown at 37° C. in RHAF broth to an $O.D_{660}$ of 0.6–0.8 and harvested by centrifugation. The cell pellet is resuspended in 1/10 volume of HAF protoplasting buffer and lysozyme is added to a final concentration of 200 ug/ml. This is incubated at 37° until 90–100% protoplast formation is achieved. The protoplasts are pelleted and washed once with RHAF broth. They are then resuspended in 1/25 the original culture volume of RHAF. DNA (1–5 ug) is added to an aliquot of protopiasts (0.5 ml) immediately followed by the addition of 30% PEG in HAF buffer (1.5 ml) and incubated at room temperature for five minutes. RHAF (5 ml) is then added, and the protoplasts pelleted. The pellets are resuspended in RHAF (0.5 ml), and aliquots (100 ul each) are plated on RHAF plates and incubated at 30° C. After 18 hours, these plates are replica plated using Repli-plates (FMC) to SNB plates containing the selective antibiotic, and incubated for 24 hours at 30° C. Single isolated transformants are then picked for further testing.

Colony Hybridization

Cell transformants are patched on solid agar plates and incubated at 30° C. for 16 to 24 hours. A nitrocellulose filter placed over the colonies is removed, the colonies lysed by floating the filter on a pool of lysozyme solution in TES buffer (2 mg/ml) at 37° for thirty minutes, and then filters serially transferred to petri dishes containing denaturation buffer (0.5M NaOH, 2.5M NaCl) for ten minutes, and neutralization buffer (0.5M Tris, 3M NaCl) for ten minutes. They are then rinsed for five minutes with 2× SSC (1× SSC is 0.15M NaCl plus 0.015M sodium citrate) and baked at 80° C. for two hours. They are then prehybridized in a solution containing 50% formamide, 5×Denhardt solution (Denhardt, A Membrane Filter Technique For The Detection of Complementary DNA, Biochem. Biophys. Res. Commun. 23 64–646), 5×SSPE (0.18M NaCl, 0.01M sodium $PP_i$, 1 mM EDTA), 0.1% SDS, and 125 ug/ml of calf thymus DNA for two hours aT 42° C. in a sealable plastic bag.[2] A 15-ml sample of prehybridization buffer is removed, a suitable nick-translated probe is added, and incubation continued at 42° C., for 15 hours. The filters are washed free of the probe by repeated washings with 1× SSPE+0.1% SDS. Air-dried filters are then exposed to Kodak X-Omat film.

[2] Concentration when expressed as percentages in this specification is weight per volume, namely g/100 ml.

Fermentation of Transformed *B. megaterium*

Figure 7:
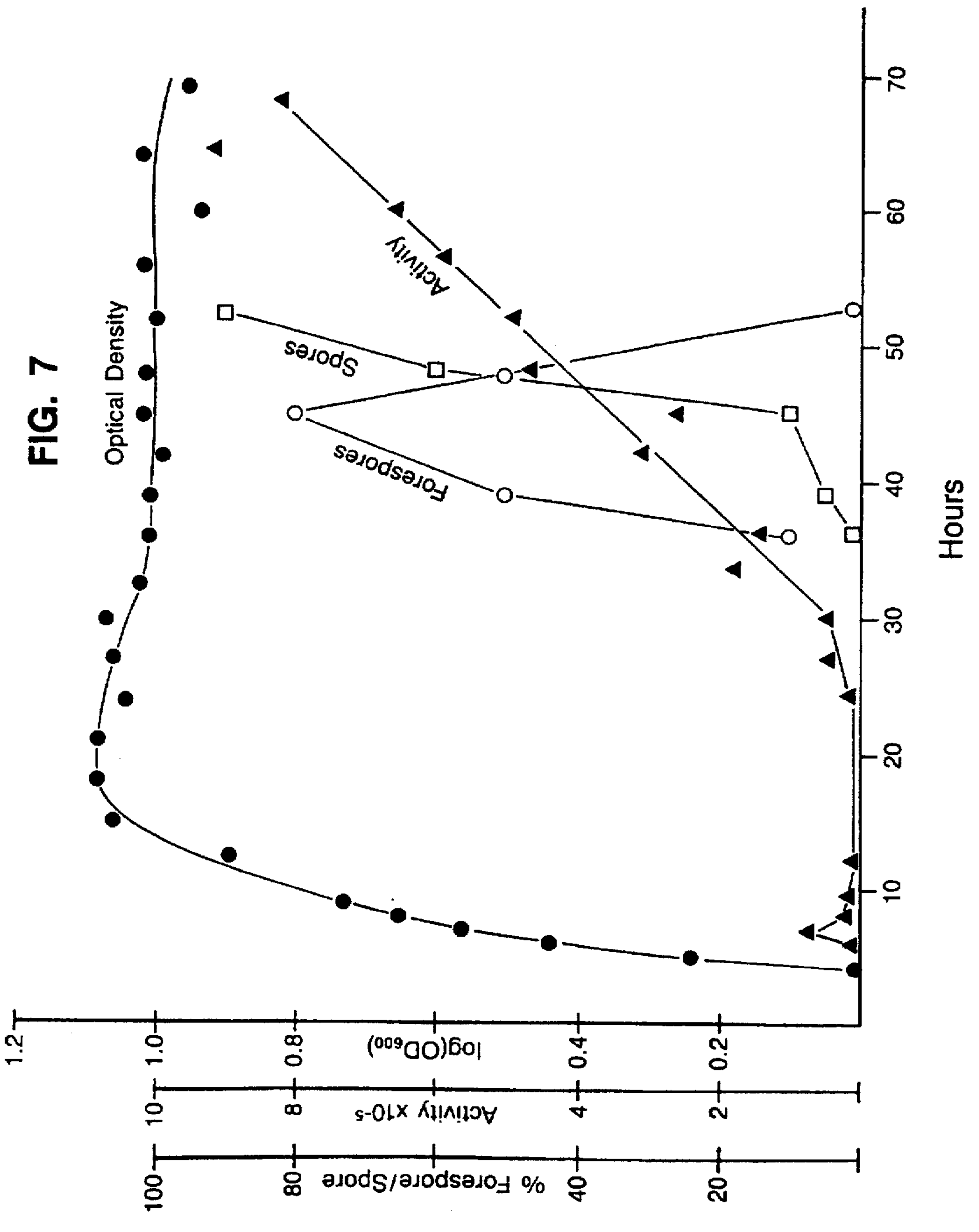
FIG. 7 is a graph illustrating antigen activity in the cell extracts of ABM10 grown in a 10 L fermentor for various periods. Forespore (0—0) and spore (□—□) counts were determined by microscopic observation. The gp41 antigen activity in the cellular extracts (▲—▲) was determined as described in the Methods. Optical density (●—●) was determined in a spectrophotometer.

Transformed *B. megaterium* is grown in a rich media (2% Soytone (Difco.), 3.3% soluble starch, 0.24% $K_2HPO_4$, 0.1% $KH_2PO_4$, 0.1% $(NH_4)_2SO_4$, 0.05% $MgSO_4$, $7H_2O$, 0.05% Antifoam and the appropriate antibiotic) for twenty hours. These cells are used to inoculate a ten liter fermentor containing rich media (the same as above) in which the cells are grown for twenty to ninety six hours (preferably sixty to eighty hours) until the culture is in its sporulation phase. As shown in FIG. 7 for production of HIV-I gp41-BM in ABM10 (Example 18), as the spores are being formed, the activity of 41spf-1 concomitantly increases.

A New Brunswick Gen II Microgen Fermentor (600 rpm agitation, 5 SLPM air flow, 5 psi head pressure, pH controlled at 7.0) was used. The temperature was maintained at 22–42 degrees centigrade (preferably 25 degrees centigrade) during fermentation. The appropriate antibiotic was added to the fermentor before inoculation to allow only the appropriate cells to propagate. Cells were harvested by centrifugation as described in the following examples.

Fermentation was carried out in a glucose reduced media, preferably having a glucose concentration from zero to about 0.1%.

Preparation of cell extracts for protein analysis.

Cells grown as described above are sedimented at 10,000×g. The cells lysed with lysozyme (1 mg per ml in TESP (30 mM Tris hydrochloride [pH 7.6], 5 mM EDTA, 50 mM NaCl, 2 mM phenylmethylsulfonyl fluoride)) and DNAse (20 ug/ml), and the cells are mixed with an equal volume of sample buffer (4% SDS, 20% glycerol, 10% B-mercaptoethanol, 8M urea, 0.125M Tris hydrochloride [pH 6.8]), boiled for ten minutes, cooled, and sedimented at 15,000×g. The clear supernatant is analyzed for proteins by SDS-polyacryiamide gel electrophoresis.

Immunological detection of HIV-1 Envelope protein 41spf-1.

The proteins produced in bacterial clones are resolved on a 12% or 15% SDS-polyacrylamide gel by electrophoresis and then transferred electrophoretically to nitrocellulose (NC) sheets. These sheets are soaked in blocking solution (1% gelatin, 1% casein hydrolysate, 5% Tween-20 in TBS-T buffer consisting of 20 ml Tris-HCl, pH 7.4, 500 mM NaCl, and 0.01% Thimerisol) and placed on a rocking platform at room temperature (RT) for thirty minutes. The blocking solution is discarded, and the NC sheets are serially washed with TBS-T, PBST (20 mM $NaH_2PO_4$, pH 7.4, 150 mM NaCl, 0.05% Tween-20) and TBS-T. Monoclonal antibody for HIV-1 envelope protein gp41, referred to as anti-p41, diluted in antibody buffer (20 mM NaH$_2$PO$_4$, pH 7.4, 500 mM NaCl, 0.05% Tween-20, 1% BSA) is then added to the NC sheets and rocked at room temperature for about four hours. The NC sheets are washed serially with TBS-T, PBST and TBS-T as before to remove the unbound antibody. Goat anti-mouse antibody (Kirkegaard and Perry Labs, Inc., Gaithersburg, Md. Catalog #011806) diluted in antibody buffer is then added to the NC sheets and rocked at room temperature for four hours. After the three washes as before, the NC sheets are treated with rabbit anti-goat IgG-horseradish peroxidase (Kirkegaard and Perry Labs, Inc., Gaithersburg, Md. Catalog #141306) for 2–4 hours. The NC sheets are washed as before and 20 ml of the color development reaction mixture (30 mg HRPO substrate [4-chloro-1-naphthol] in 10 ml cold methanol to which 120 ul of hydrogen peroxide in 50 ml PBS is added just prior to use) is poured over the NC sheets. A purple color develops usually within 15 minutes to give a positive signal.

Assay for p41 Antigen (Bead Assay)

Cellular extracts are diluted 1:4 in a urea-preincubation buffer (20 mM ethanolamine, 7M urea, 5 mM DTT, 0.1% Tween-20, pH 11.0) and incubated for 60 minutes at 25° C. After further dilutions of 1:10, 1:50, 1:100, 1:500 in a sample diluent (20 mM ethanolamine, 10% newborn calf serum, 10 mM EDTA, 0.2% Tween-20, 2M urea, 0.2M NaCl, 0.1% NaN$_3$, 4 mg/ml bromphenol blue, pH 9.0), 200 ul of each diluted sample is added to wells of a bead assay plate (Abbott Laboratories #93-0883). A 0.25 inch diameter bead containing antibody to the gp41 antigen bound to its surface (Abbott Laboratories #4234A) is added to each well, and the assay plate is incubated at 40° C. for sixty minutes. Bead/wells are washed three times with water, and 200 ul of iodinated monoclonal anti-gp41 antibody (diluted in sample diluent minus the urea, to a concentration of 3.4 uCi/ml) is added to each well. The assay plates are incubated at 40° C. for sixty minutes, and the bead/wells are washed three times with water. The beads are transferred to vials, and radioactivity levels determined. Known amounts of the gp41 antigen (7–225 Units) are added to separate wells to develop a standard assay curve while sample diluent alone defines the negative background level. A unit of gp41 antigen activity represents an arbitrary amount of antigen which in this assay gives a clear signal level. Increasing unit levels represent increasing antigen levels.

Some of the general methods that were used in carrying out the present invention are described above or referenced in this section or elsewhere in the text.

MEDIA USED

SNB medium:

SNB media consists of solutions A and B.

Solution A consists of 8 ml SNB salts (0.05 mM FeSO$_4$, 1 mM MnCl$_2$, 5% KCl and 50 mM MgSO$_4$.7H$_2$O ), 8 g Nutrient Broth (Difco Laboratories, Detroit, Mich.), 15 g Bacto-Certified Agar (Difco) and 900 ml glass distilled deionized water. Solution B (100 ul) consists of 10 mM CaCl$_2$.2H$_2$O, and 1% glucose in glass distilled deionized water. Solutions A and B are autoclaved separately, and combined when cool.

RHAF BROTH:

RHAF broth consists of media made from solutions C and D. Solution C is 5 g yeast extract, 5 g Tryprone and 500 ml glass distilled deionized water. Solution D is made from 12 g Tris base, 2.0 g glucose, 68.5 g sucrose, 0.14 g KH$^2$PO$_4$, 10 ml HAF salts (0.35 g KCl, 0.58 g NaCl, 1.3 g Na$_2$SO$_4$, 10.0 g NH$_4$Cl and 100 ml distilled deionized water), and 470 ml distilled deionized water. Solutions C and D are autoclaved separately, mixed when cool and 10 ml of 2M MgCl$_2$ is added.

HAF PROTOPLASTING BUFFER:

HAF protoplasting buffer consists of 12.0 g Tris-base, 68.5 g sucrose, 10 ml HAF salts, 980 ml ddH$_2$O and titrated to pH 7.5, autoclaved, cooled and 10 ml of 2M MgCl$_2$ is added.

EXAMPLES

Example 1

Construction of plasmid pAS5

Approximately 2 ug of the plasmid pE194 was linearized by digestion with the enzyme XbaI, under standard conditions. The digested DNA was extracted with phenol-chloroform and precipitated in ethanol. The DNA was treated with E. coli DNA polymerase I under standard conditions to fill in the 3' ends of the DNA fragments. This was then mixed with about 1 ug of the plasmid pVG1 (see FIG. 11) that had been linearized by digestion with the restriction enzyme SmaI and purified according to standard conditions. The mixture of DNAs were then incubated at 14° C. for 16 hours in the standard blunt end ligation buffer containing T4 DNA ligase. The reaction mixture contained the plasmid pAS5.

Example 2

Construction of B. subtilis DB104/pAS5

Approximately one-tenth of the ligation mixture from Example 1, was used to transform E. coli K12 TB-1 cells under standard conditions employing selection for ampicillin resistance on LB-agar plates. The resultant transformants were scraped from the agar plates into the lysis buffer and plasmid DNA prepared was used to transform competent B. subtilis DB104 cells employing selection for erythromycin resistance. Several of the transformants were selected, plasmid preparations made and analyzed by restriction enzyme analysis. One such transformant DB104/pAS5 which showed the correct plasmid size with the correct restriction pattern was designated as ABS108.

Example 3

Construction of plasmid pAS14

Approximately 2 ug of plasmid PAS5, isolated from B. subtilis strain ABS108 (Example 2) was linearized by digestion with the restriction enzyme SalI under standard conditions. The digested DNA was purified and the 3' ends were filled in using E. coli DNA polymerase I as described in Example 1.

Separately, about 2 ug of the recombinant plasmid p41C isolated from an E. coli clone was treated with the restriction enzyme EcoRI under standard conditions. DNA extracted with phenol-chloroform and precipitated in ethanol. The DNA pellet was dissolved in TE buffer and further digested with restriction enzyme SalI under standard conditions. The digested DNA was purified by phenol-chloroform extraction and ethanol precipitation. EcoRI and SalI double digested DNA was then treated with E. coli DNA polymerase I as before. Next, about 100 ng of pAS5/SalI-Klenow digest was mixed with about 800 ng of p41C/EcoRI-SalI-Klenow digest and ligated with T4 DNA ligase at 14° C. for 16 hours. The reaction mixture at this stage contained pAS14 DNA.

Example 4

Construction of *B. subtilis* DB104/pAS14

About one-tenth of the digestion mixture containing pAS14 (Example 3) was used to transform *E. coli* K12 TB-1 cells (obtained from T. Baldwin, Texas A & M University) under standard conditions employing selection for ampicillin resistance on LB-agar plates. The resultant transformants were scraped from the agar plates into the lysis buffer, and the plasmid DNA prepared was used to transform competent *B. subtilis* DB104 cells employing selection for erythromycin resistance on TBAB-agar (Difco.) plates. The resultant colonies were then screened by colony hybridization using an internal DNA fragment of the HIV-1 env gene that was $^{32}$P-labelled by nick translation as the probe. The plasmid DNA prepared from several of the positives, thus identified, were analyzed by restriction enzyme analysis. One such transformant DB104/pAS14 was designated as ABS120. The physical map of the plasmid pAS14 is shown in FIG. 2.

Example 5

Expression of the protein 41spf-1 in *B. subtilis* ABS120.

ABS120 was grown overnight at 30° in 2×SG sporulation medium (nutrient broth 16 g/l, $MgSO_4.7H_2O$ 0.5 g/l, KCl 2 g/l, $Ca(NO_3)_2$ $10^{-3}$M, $MnCl_2$ $10^{-4}$M, $FeSO_4$ $10^{-6}$M, glucose 0.1%) containing 5 ug/ml erythromycin, for 12 hours, and isolated after a 100 fold dilution into the same medium and growth was monitored in a Klett Summerson colorimeter. A 10 ml sample was removed four hours after stationary phase had been reached and processed for protein preparation as described in General Methods. The proteins were analyzed by SDS polyacrylamide gel electrophoresis.

Figure 3:
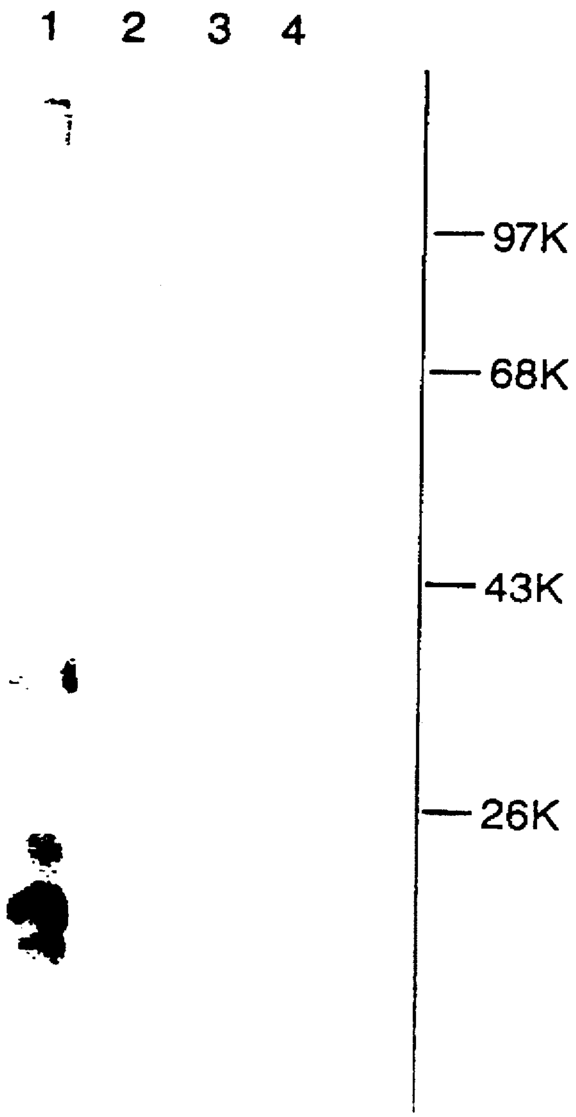
FIG. 3 is a Western blot of the proteins made in *B. subtilis* ABS120 reacting to the antibody for gp41. Lane 1 shows the protein from *E. coli*/p41C as a control. Lanes 3 and 4 show proteins of the pellet from the lysate of ABS120, extracted with 8M urea and 1% SDS, respective. Lane 2 shows the prestained molecular weight standards.

FIG. 3 shows a Western blot of the proteins. Lane 2 shows the prestained protein standards. Lanes 3 and 4 show proteins from ABS120, reacting with the antibody for the HIV-1 transmembrane envelope protein gp41. For comparison, the antibody reactive protein from *E. coli*/p41C is shown on lane 1. Proteins from the parent strain of *B. subtilis* containing the vector only, were resolved on lane 5. A protein of about 41,000 molecular weight reacted with the gp41 antibody. Compared to *E. coli*, negligible degradation of gp41 was noticed in *B. subtilis*.

The plasmid pAS14 from ABS120 (Example 4) was subcloned as HindIII-HindIII, HindIII-BamHI, or BamHI-BamHI fragments into M13mp18 and M13mp19 vectors[3]. The DNA sequence reaction protocols were carried out according to Tabor et al.[4] Gel electrophoresis was performed with modifications as reported by Barker et al.[5] Reverse orientations of the fragments were sequenced to assure accuracy of sequence data generated. The fusion of this sequence with the spoVG regulatory region was in proper order so as to give a correct translational fusion.

[3] Messing J., 1983, "New M13 Vectors for Cloning", *Meth. Enzymol*, 101:20–78

[4] Tabor S. and C. C. Richardson, 1987, "DNA Sequence Analysis With a Modified Bacteriophage T7 DNA Polymerase", *Proc. Natl. Acad. Sci. USA*, 84:4767–4771

[5] Barker R. F., Idler K. B., Thompson D. V., Kemp J. D., *Plant Mol. Biol.*, 2:335–350 (1983)

Example 6

Construction of *Bacillus megaterium* PV361/pAS14

The plasmid DNA pAS14 prepared from ABS120 was introduced into *B. megaterium* PV361 by protoplast transformation employing selection for erythromycin resistance as described in General Methods. The transformants that were picked were screened for the correct plasmid size and restriction sites by standard protocols. One such transformant PV361/pAS14 was designated as ABM10. This cell line has been deposited under the Budapest Treaty at Northern Regional Research Laboratory USDA Peoria, Ill. U.S.A. under USDA accession number NRRL B-18323.

Example 7

Construction of *Bacillus megaterium* BGSC 7A8/pAS14

The plasmid DNA pAS14 prepared from ABS120 was introduced into *B. megaterium* BGSC7A8 ($arg^-met^-$) by protoplast transformation employing selection for erythromycin resistance as described in General Methods. The transformants that were picked were screened for the correct plasmid size and restriction sites by standard protocols. One such transformant BGSC 7A8/pAS14 was designated as ABM13. This cell line has been deposited under the Budapest Treaty at Northern Regional Research Laboratory USDA Peoria, Ill. U.S.A. under USDA accession number NRRL B-18324.

Example 8

Construction of *Bacillus megaterium* QMB 1551/pAS14

The plasmid DNA pAS14 prepared from ABS120 was introduced into *B. megaterium* QMB1551 by protoplast transformation employing selection for erythromycin resistance as described in General Methods. The transformants that were picked were screened for the correct plasmid size and restriction sites by standard protocols. One such transformant QMB 1551/pAS14 was designated as ABM14.

Example 9

Expression of the protein 41sof-1 in *B. megaterium* ABM10

*B. megaterium* strain ABM10 was grown overnight at 30° C. in LB medium containing erythromycin at 5 ug/ml concentration and subcultured by 100 fold dilution into the same medium and grown at 30° C. Aliquots were removed at different times and processed for protein preparations as described in General Methods.

Figure 4:
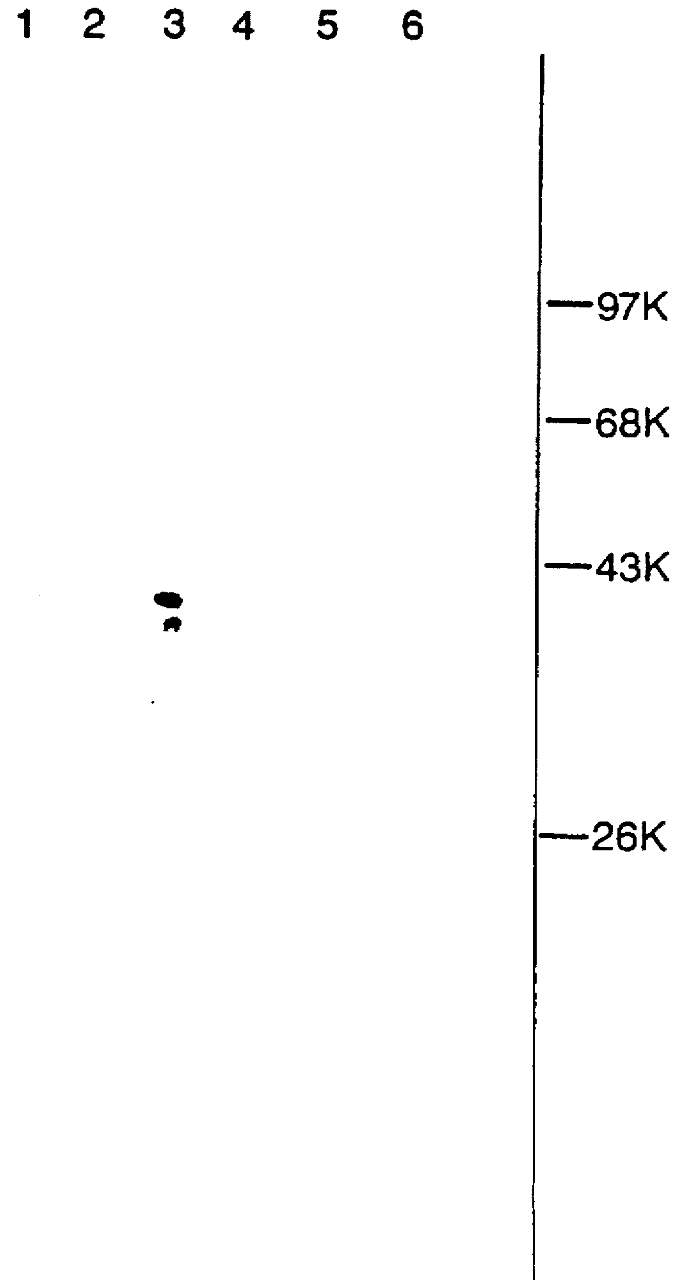
FIG. 4 is a Western blot of proteins made in *B. megaterium* strains ABM10, ABM11 and ABM12, reacting to the antibody for gp41. Lanes 1 and 6 show the prestained molecular weight protein standards. Lane 2 shows the proteins from the parent strain PV361 as a control. Lanes 3, 4 and 5 show the proteins from ABM10, ABM11 and ABM12 respectively.

FIG. 4 shows a Western blot of the proteins separated by SDS-polyacrylamide gel electrophoresis. Lanes 1 and 6 show the prestained molecular weight standards. Lanes 2 and 3 show proteins from the parent strain PV361 and ABM10 respectively. ABM13 and ABM14 also produced 41spf-1 proteins that were reactive to gp41 antibody on Western blots (not shown).

Example 10

Construction of plasmid pCR2

Approximately 2 ug of the plasmid pAS14, isolated from *B. subtilis* strain ABS120 and purified on CsCl-EtBr density gradients, was serially digested with the restriction enzymes ClaI, EcoRI and SmaI, under standard conditions.

The restriction fragments of DNA were separated by electrophoresis on 0.8% agarose horizontal gels. A 4.2 kb fragment, containing the plasmid pVG1 with the gene for gp41 linked to the spoVG promoter, was cut out from the gel, and DNA was eluted electrophoretically. The eluted DNA was further purified by loading and eluting through a ELUTIP-D column and concentrating by ethanol precipitation. The sticky ends generated in this fragment were filled in using *E. coli* DNA polymerase I (Klenow), under standard conditions. This fragment is referred to as Fragment "A". Approximately 2 ug of the plasmid pUB110 was serially digested with the restriction enzymes EcoRI and PvuII, under standard conditions. The restriction fragments were separated as before on a 0.8% agarose gel by electrophoresis, and a 3.5 kb fragment comprising a *Bacillus subtilis* replication origin and a kanamycin resistance conferring gene was isolated, treated with *E. coli* DNA polymerase I and purified as before. This is referred to as fragment B.

Approximately, equal amounts of fragment "A" and fragment "B" were mixed in a standard blunt end ligation reaction mixture containing T4 DNA ligase and incubated at 14° C. for 16 hours. The reaction mixture at this stage contained the plasmid pCR2.

Example 11

Construction of *Bacillus megaterium* PV361/pCR2

Approximately, one-tenth of the reaction mixture containing pCR2 (Example 10) was used to transform *E. coli* K12 TB-1 cells under standard conditions employing selection for ampicillin resistance on LB-agar plates. The resultant ampicillin resistant colonies were scraped from the agar plates into the lysis buffer, and the plasmid DNA prepared was introduced into *B. megaterium* PV361 by protoplast transformation as described in General Methods. The transformants picked by employing selection for kanamycin resistance at 5 ug/ml concentration were sorted by mini screening for proper plasmid sizes and by Western blot analysis employing antibodies specific for the HIV-I transmembrane envelope protein gp41. One such transformant *B. megaterium* strain PV361/pCR2 is designated as ABM11. The physical map of plasmid pCR2 is shown in FIG. 5.

Example 12

Expression of the protein 41spf-1 in *B. megaterium* ABM11.

*B. megaterium* strain ABM11 was grown overnight at 30° C. in LB medium containing kanamycin at 5 ug/ml concentration and subcultured by 100 fold dilution into the same medium and grown at 30° C. Aliquots are removed at different times and processed for protein preparations as described in General Methods.

FIG. 4 shows a Western blot of the proteins separated by SDS-polyacrylamide gel electrophoresis. Lanes 1 and 6 show the prestained protein standards. Lanes 2 and 4 show the proteins from the parent strain PV361 and ABM11 respectively.

Example 13

Construction of plasmid pCR5

Approximately 2 ug of plasmid pC194 (Horinouchi and Weisblum, Control of Gene Expression and Replication in Plasmids pE194 and pC194. In: A. T. Ganesan et al. (eds.) Molecular Cloning and Gene Regulation in Bacilli. Academic Press, New York PP. 287–310 (1982)) was digested with the restriction enzymes DraI and ClaI under standard conditions. The restricted DNA fragments were separated on a 0.8% agarose gel by electrophoresis, and a 1108 bp fragment containing the chloramphenicol acetyl transferase (cat) gene was isolated and purified as described in Example 8. This is referred to as fragment "A".

Approximately 1 ug of plasmid pAS14 was serially digested with ClaI and SmaI under standard conditions. The restricted DNA fragments were separated on a 0.8% agarose gel by electrophoresis, and a 6416 bp fragment containing the origin of replication of pE194 and the entire p41C gene, but missing the gene for erythromycin resistance, was isolated and purified as in Example 1. This is referred to as fragment Approximately, equal amounts of fragment "A" and fragment "B" were mixed in a standard ligation reaction mixture containing T4 DNA ligase and incubated at 14° C. for 16 hours. The reaction mixture at this stage contained the plasmid pCR5 (FIG. 6).

Example 14

Construction of *Bacillus megaterium* PV361/pCR5

Approximately, one-tenth of the reaction mixture containing pCR5 (Example 11) was used to transform *E. coli* K12 TB-1 cells under standard conditions employing selection for ampicillin resistance on LB-agar plates. The resultant ampicillin resistant colonies were scraped from the agar plates into the lysis buffer, and the plasmid DNA prepared was introduced into *B. megaterium* PV361 by protoplast transformation as described in General Methods. The transformants were picked by employing selection for chloramphenicol resistance (at 5 ug/ml concentration) and were sorted by mini-screening for correct plasmid sizes and by Western blot analysis employing antibodies specific for the HIV-1 transmembrane envelope protein. One such transformant PV36t/pCR5, that satisfied both the criterion is designated ABM12. This cell line has been deposited under the Budapest Treaty at Northern Regional Research Laboratory USDA Peoria, Ill. U.S.A. under USDA accession number NRRL B-18325. The physical map of plasmid pCR5 is shown in FIG. 6.

Example 15

Construction of *B. megaterium* BGSC 7A8/pCR5

Approximately 1 ug of the plasmid pCR5 purified from *B. megaterium* ABM12 was introduced into *B. megaterium* BGSC 7A8 by protoplast transformation employing selection for chloramphenicol resistance as described in General Methods. The transformants that were picked were screened for the correct plasmid size and restriction sites by standard protocols. One such transformant BGSC 7A8/pCR5 was designated as ABM15. This cell line has been deposited under the Budapest Treaty at Northern Regional Research Laboratory USDA Peoria, Ill. U.S.A. under USDA accession number NRRL B-18326.

Example 16

Construction of *B. megaterium* QMB 1551/pCR5

Approximately 1 ug of the plasmid pCR5 purified from *B. megaterium* ABM12 was introduced into *B. megaterium* QMB 1551 by protoplast transformation employing selection for chloramphenicol resistance as described in General Methods. The transformants that were picked were screened for the correct plasmid size and restriction sites by standard protocols. One such transformant QMB 1551/pCR5 was designated as ABM16.

Example 17

Expression of the protein 41spf-1 in *B. megaterium* ABM12.

*B. megaterium* strain ABM12 was grown overnight at 30° C. in LB medium containing chloramphenicol at 5 ug/ml concentration and were subcultured by 100 fold dilution into the same medium and grown at 30° C. Aliquots were removed at different times and processed for protein preparations as described in General Methods.

FIG. 4 shows a Western blot of the ABM12-expressed proteins separated by SDS-polyacrylamide gel electrophoresis. Lanes 1 and 6 show the prestained molecular weight standards. Lanes 2 and 5 show the proteins from the parent strain pV361 and ABM12 respectively. ABM15 and ABM16 also produced proteins that were reactive to gp41 antibody on Western blots (not shown).

Example 18

Fermentative production of the protein 41spf-1 from *B. megaterium* strain ABM10.

An overnight culture of ABM10 was grown in a rich fermentation medium (see general methods) containing 5 ug/ml erythromycin, in the absence of glucose for twenty hours at 30° C. and subcultured by a 100 fold dilution into ten liters of the same medium and grown in a fermentor. Aliquots removed at different time intervals were processed for protein preparations as described in General Methods.

These preparations were used to visualize the gp41 protein by Western blotting analysis and to quantitate the binding activity to the beads coated with the monoclonal antibodies to gp41. The spore and forespore counts were estimated by spectrophotometric observation. FIG. 7 depicts graphically the antibody binding activity in the cell extracts of ABM10. As discussed previously, the activity of 41spf-1 (as measured by HIV-I gp41 antibody binding) in the cell extracts increases as the cells begin to sporulate in the stationary phase of the growth cycle. In FIG. 7, the gp41 activity increased starting at about 24 hours and increased steadily until at least 70 hours after fermentation was begun.

Figure 8:
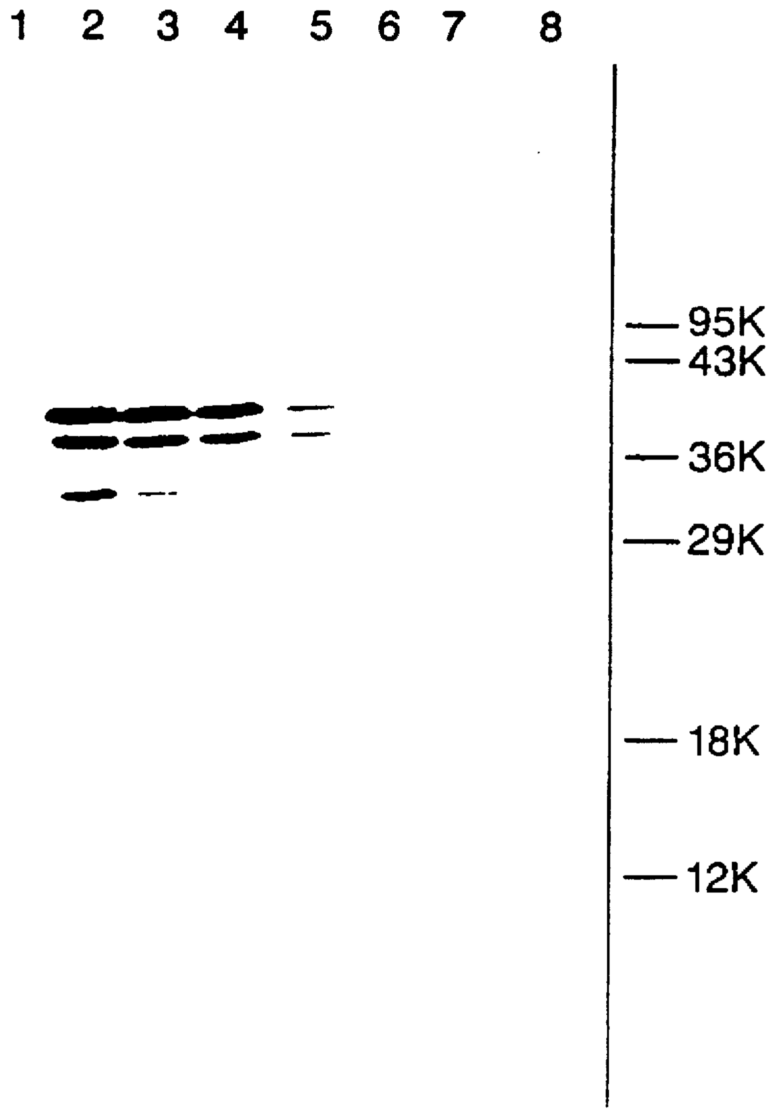
FIG. 8 is a Western blot of the proteins expressed by *B. megaterium* ABM10 grown in a 10 L fermentor. Lanes 1 and 8 show protein standards. Proteins from cultures grown for 72 hours (lane 2), 56 hours (lane 3), 48 hours (lane 4), 32 hours (lane 5), 24 hours (lane 6) and 8 hours (lane 7) that were recognized by the antibodies for gp41. Extracts from 1.25 mg (wet weight) of cells were loaded in each well.

FIG. 8 shows a Western blot of the proteins from ABM10 grown in a ten liter fermentor. Aliquots were removed at various times, processed for protein preparations and separated on a 15% SDS-polyacrylamide gel by electrophoresis. The proteins reactive to gp41 antibody were visualized from 24 hours onwards, the level increasing steadily with time up to 72 hours after fermentation was begun.

Example 19

Fermentative production of the protein 41spf-1 from *B. megaterium* ABM11.

An overnight culture of ABM11 was grown in a rich fermentation medium containing 5 ug/ml kanamycin in the absence of glucose for twenty hours at 30° C. It was subcultured by a 100 fold dilution into ten liters of the same medium and grown in a fermentor. Aliquots removed at different time intervals were processed for protein preparations as described in General Methods. These preparations were used to visualize the 41spf-1 protein by Western blotting analysis.

Figure 9:
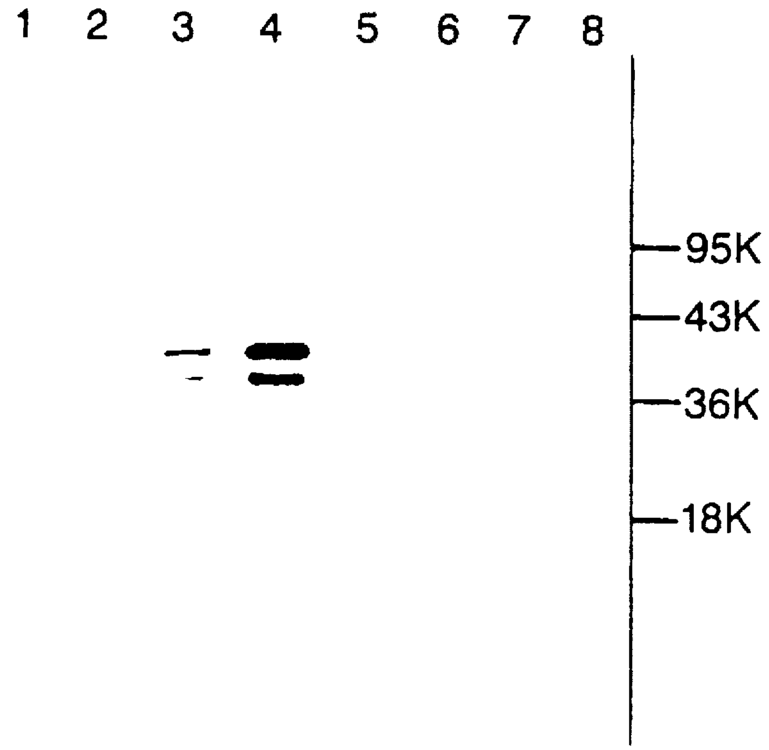
FIG. 9 is a Western blot of the proteins expressed by *B. megaterium* ABM11 and ABM12 grown in 10 L fermentors. Lanes 1 and 5 show protein standards. Lanes 2, 3 and 4 show proteins from ABM12 at 24, 48 and 72 hours reactive to antibodies for gp41. Lanes 6, 7 and 8 show proteins from ABM11 at 20, 44 and 68 hours, reactive to antibodies for gp41. Extracts from 2.5 mg wet weight of cells were loaded in each well.

FIG. 9 shows a Western blot of the proteins from ABM11 grown in a 10 L fermentor. Aliquots were removed at various times, processed for protein preparations and separated on a 15% SDS polyacrylamide gel by electrophoresis. Lanes 6, 7 and 8 show proteins, reactive to gp41 antibody, removed from the fermenter 20, 44 and 68 hours after fermentation was begun. Very little activity was apparent from this construct when grown under fermentation conditions.

Example 20

Fermentative production of the protein 41spf-1 from *B. megaterium* ABM12.

An overnight culture of ABM12 was grown in a rich fermentation medium containing 10 ug/ml chloramphenicol in the absence of glucose for 20 hours at 30° C. and was subcultured by a 100 fold dilution into ten liters of the same medium, and grown in a fermentor at 25 degrees centigrade for 72 hours. Aliquots removed at various times were processed for protein preparations as described in General Methods. These preparations were used to visualize the gp41-BM protein by Western blotting analysis.

FIG. 9 shows a Western blot of the proteins from ABM12 grown in a ten liter fermentor. Aliquots removed from the fermentor at 24, 48 and 72 hours after fermentation was begun were processed for protein preparation and separated on a 15% SDS-polyacrylamide gel by electrophoresis as shown in lanes 2, 3, and 4, respectively. These proteins were reactive to antibodies to HIV gp41. Thus, The concentration of proteins reactive to gp41 antibody in the fermentation media increased with fermentation time.

Example 21

Purification of 41spf-1 protein

*B. megaterium* pCR5/PV361 cells (ABM 12) from Example 14 were harvested after 76 hours of fermentation and stored frozen at −70° C. 15 grams of cells were thawed and 21 ml of buffer consisting of 10 mM Tris, pH 8.0, 1 mM EDTA, and 15 mM $MgCl_2$ were added followed by 1.8 milliliters of a solution of 10 mg/ml lysozyme and 100 microliters of a solution of 1 mg/ml DNase I in the same buffer. The resulting slurry was mixed well, then incubated at 37 degrees centigrade for thirty minutes to induce lysis of the cells. The lysate was centrifuged at 19,000 rpm for thirty minutes in a Sorvall SS-34 rotor at 4 degrees centigrade, and the supernatant was decanted and discarded.

The pellet was suspended in approximately ten milliliters of 0.25M Tris, pH 7.0 using a homogenizer. Triton X-100 (1.75 ml) was added, and the total volume adjusted to 35 ml with 0.25M Tris, pH 7.0. The pellet suspension was gently rocked for one hour at 2–8 degrees centigrade, then centrifuged as above. The supernatant was discarded, and the Triton wash process was repeated on the pellet. The pellet was then washed in a similar manner with 0.25M Tris, pH 7.0 followed by 1.5% sodium deoxycholate in 50 mM Tris, pH 8.5, and again with 0.25M Tris, pH 7.0. Urea (12.61 g) was added to the pellet followed by approximately 20 ml of 0.25M Tris, pH 7.0, and this suspension quickly homogenized. The volume was adjusted to 35 ml with 0.25M Tris, pH 7.0. The pellet suspension in the urea solution was rocked overnight at 2–8 degrees centigrade, then centrifuged as above. The urea wash was repeated on the pellet with a two hour incubation time. After centrifugation, the pellet was solubilized in a solution consisting of 8M urea, 1% beta-mercaptoethanol, 0.5% SDS, and 50 mM sodium phosphate pH 6.8 by shaking overnight at 40 degrees centigrade. The solution was centrifuged as above at room temperature, and the supernatant fraction taken.

The solubilized antigen may be used directly or further purified by hydroxylapatite chromatography at 40 degrees centigrade. The column is equilibrated with 100 mM sodium phosphate, pH 7.0, 0.1% SDS. The antigen is loaded directly in the solubilization solution, and after further washing with the equilibration buffer, the elution is performed with a gradient to 500 mM sodium phosphate, pH 7.0, 0.1% SDS. The antigen elutes at a phosphate concentration of 300 mM–400 mM.

Amino acid sequencing was performed on 41spf-1 protein purified from *Bacillus megaterium* containing The plasmid pCR5. The material was purified as described above. A mixed sequence composed of two amino acid residues at each position was obtained. The peptide sequences obtained are consistent with the existence of two translational start sites: one sequence beginning with the first methionine residue coded by the spoVG gene and the other with a methionine residue of a sequence coded by the HIV gp120 gene. A strong ribosomal binding site is readily noticeable upstream of the second methionine codon in the gp120 DNA sequence.

Example 22

Fermentative production of the protein 41spf-1 from *B. megaterium* strain ABM15.

An overnight culture of ABM15 (Example 15) was grown in a rich fermentation medium containing 5 ug/ml chloramphenicol in the absence of glucose for twenty hours at 30° C. and was subcultured by a 100 fold dilution into ten liters of the same medium and grown in a fermentor. Aliquots removed at different time intervals were processed for protein preparations as described in General Methods.

Figure 10:
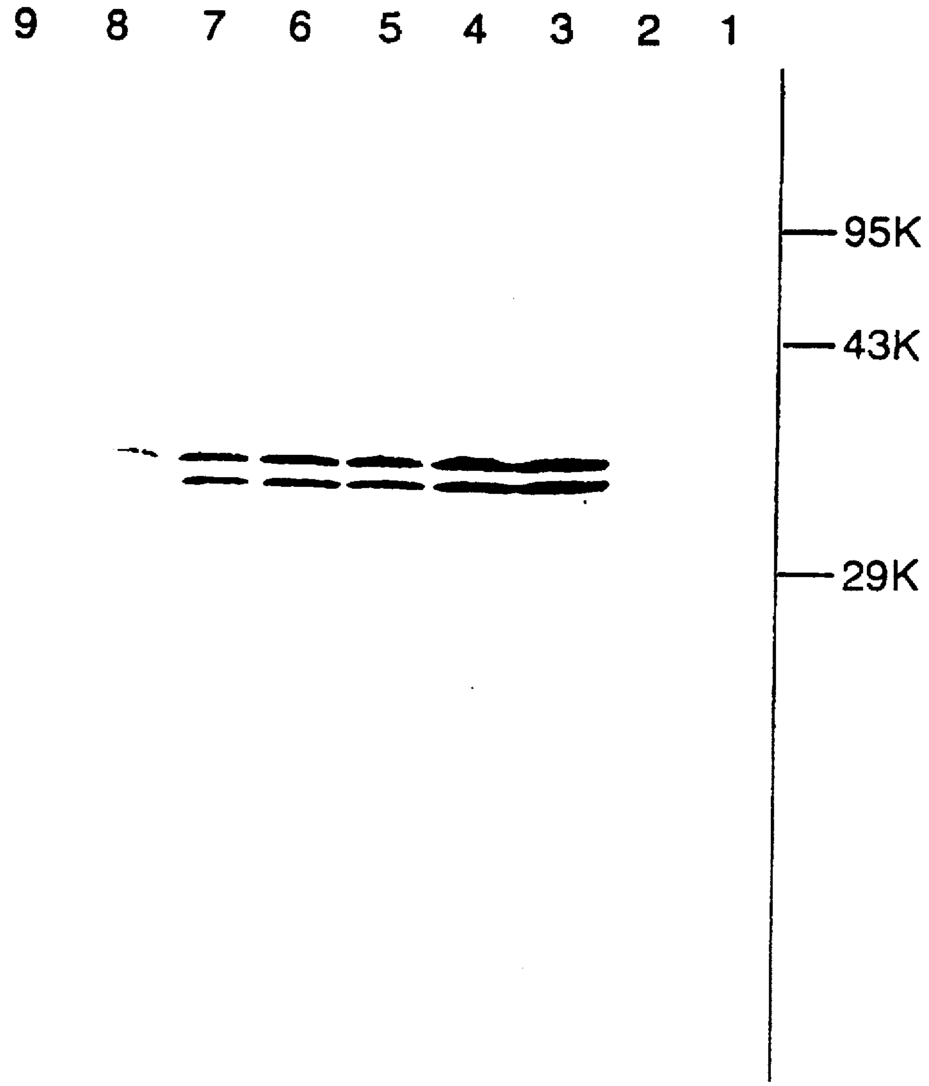
FIG. 10 is a Western blot of the proteins expressed by *B. megaterium* ABM15. Lane 1 shows the prestained protein markers. Lanes 2–9 show proteins reactive to HIV-I gp41 antibody obtained from aliquots removed from the fermentation media at 8, 20, 32, 44, 56, 68, 80, and 92 hours respectively after fermentation was begun.

These preparations were used to visualize the 41spf-1 protein by Western blotting analysis. FIG. 10 shows a Western blot of the proteins from ABM10 grown in a ten liter fermentor. Aliquots removed at 8, 20, 32, 44, 56, 68, 80, and 92 hours after fermentation was begun were processed for protein preparations and separated on a 15% SDS-polyacrylamide gel by electrophoresis as shown in lanes 2–9, respectively. The proteins reactive to gp41 antibody were produced primarily between 8 and 32 hours.

We claim:

1. A method of expressing a heterologous HIV protein in recoverable form in *Bacillus megaterium*, said method comprising the steps of:

(a) introducing into *Bacillus megaterium* a DNA sequence including the spoVG sporulation promoter of *Bacillus subtilis*, and a structural gene encoding said heterologous HIV protein under the control of said spoVG promoter, wherein said structural gene encodes an HIV-1 gp41 protein or fragments thereof which are capable of reacting with antibodies to said HIV-1 gp41 protein;

(b) culturing said *Bacillus megaterium* under conditions in which said structural gene is expressed from said spoVG promoter; and (c) recovering said heterologous HIV protein from said *Bacillus megaterium.*

2. The method of claim 1 wherein said DNA sequence comprises plasmid DNA from *B. subtilis.*

3. The method of claim 2 wherein said plasmid DNA further includes plasmid DNA from *E. coli* fused to the plasmid DNA from *B. subtilis.*

4. The method of claim 3 wherein said plasmid DNA is selected from the group consisting of pAS14 and pCR5.

5. The method of claim 1 wherein said step of culturing includes inoculating said *Bacillus megaterium* into a growth media, and growing said *Bacillus megaterium* at least twenty hours after inoculation, then recovering said heterologous protein.

6. The method of claim 5 wherein said *Bacillus megaterium* is maintained at a temperature of from about 22 about 42 degrees centigrade while being grown.

7. The method of claim 5 wherein said *Bacillus megaterium* is grown in a medium comprising soybean hydrolysate and starch.

8. The method of claim 5 wherein said *Bacillus megaterium* is grown in a media having a glucose concentration of zero to about 0.1% (w/v).

9. The method of claim 1 wherein said step of recovering said protein is achieved by concentrating said protein from said cultured *Bacillus megaterium*, dissolving said concentrated protein in a buffer comprising urea and SDS, and recovering said dissolved protein from said buffer by chromatography.

10. The method of claim 1 wherein said structural gene corresponds to a DNA sequence of the HIV-I genome.

11. An HIV fusion protein comprising the sequence of 41spf-1 produced according to the process of claim 1.

12. *B. megaterium* cell line NRRL B-18323.

13. *B. megaterium* cell line NRRL B-18324.

14. *B. megaterium* cell line NRRL B-18325.

15. *B. megaterium* cell line NRRL B-18326.

16. A *Bacillus megaterium* cell line including a DNA sequence having a spoVG sporulation promoter from *Bacillus subtilis* and a structural gene, wherein said structural gene encodes an HIV-1 p41 protein or fragments thereof which are capable of reacting with antibodies to HIV-1 gp41 protein.

* * * * *